(12) United States Patent
Marchese, Sr. et al.

(10) Patent No.: US 7,761,970 B1
(45) Date of Patent: Jul. 27, 2010

(54) METHOD OF MANUFACTURING OF ELECTROSURGICAL IMPLEMENTS

(76) Inventors: Justin W. Marchese, Sr., 68 Prospect St., Belleville, NJ (US) 07109; John L. Scholz, 42 Forest Ridge Rd., Nyack, NY (US) 10960

(*) Notice: Subject to any disclaimer, the term of this patent is extended or adjusted under 35 U.S.C. 154(b) by 856 days.

(21) Appl. No.: 11/656,836

(22) Filed: Jan. 23, 2007

(51) Int. Cl.
*B23P 25/00* (2006.01)
*B05D 1/02* (2006.01)

(52) U.S. Cl. .................. 29/458; 29/527.2; 427/2.12; 427/420; 427/424; 606/45

(58) Field of Classification Search ............... 29/458, 29/527.1, 527.2; 427/2.12, 209, 420, 424, 427/425, 427.2, 427.3; 606/45; 30/40
See application file for complete search history.

(56) References Cited

U.S. PATENT DOCUMENTS

| | | | |
|---|---|---|---|
| 3,243,321 A | 3/1966 | Rowand | |
| 4,033,351 A | 7/1977 | Hetzel | |
| 4,074,718 A | 2/1978 | Morrison, Jr. | |
| 4,161,950 A | 7/1979 | Doss et al. | |
| 4,228,800 A * | 10/1980 | Degler et al. | 606/48 |
| 4,314,559 A | 2/1982 | Allen | |
| 4,333,467 A | 6/1982 | Domicone | |
| 4,681,105 A * | 7/1987 | Tritt | 606/52 |
| 4,785,807 A | 11/1988 | Blanch | |
| 4,800,878 A | 1/1989 | Cartmell | |
| 5,197,962 A | 3/1993 | Sansom et al. | |
| 5,693,052 A | 12/1997 | Weaver | |
| 5,800,427 A | 9/1998 | Zamba | |
| 5,925,039 A | 7/1999 | Landingham | |
| 5,925,046 A * | 7/1999 | Vogel et al. | 606/51 |
| 6,059,783 A | 5/2000 | Kirwan, Jr. | |
| 6,090,107 A | 7/2000 | Borgmeier et al. | |
| 6,132,427 A | 10/2000 | Jones et al. | |
| 6,298,550 B1 | 10/2001 | Kirwan, Jr. | |
| 6,409,725 B1 | 6/2002 | Khandkar et al. | |
| 6,511,479 B2 | 1/2003 | Gentelia et al. | |
| 6,540,745 B1 | 4/2003 | Fairbourn et al. | |
| 6,589,239 B2 | 7/2003 | Khandkar et al. | |
| 6,770,071 B2 | 8/2004 | Woloszko et al. | |

\* cited by examiner

*Primary Examiner*—Jermie E Cozart
(74) *Attorney, Agent, or Firm*—Lawrence G. Fridman

(57) ABSTRACT

A method of electrosurgical implements consists of a step of formation of an integral module consisting of a plurality of space from each other interconnected implements, arranged in such manner that a multiplicity of operational spaces are defined between facing each other narrow edges of each pair of adjacent implements. In a coating step a coating is directed normally to the broad planar sides of the implements and substantially parallel to the narrow edges of the implements arranged in the operational spaces.

20 Claims, 9 Drawing Sheets

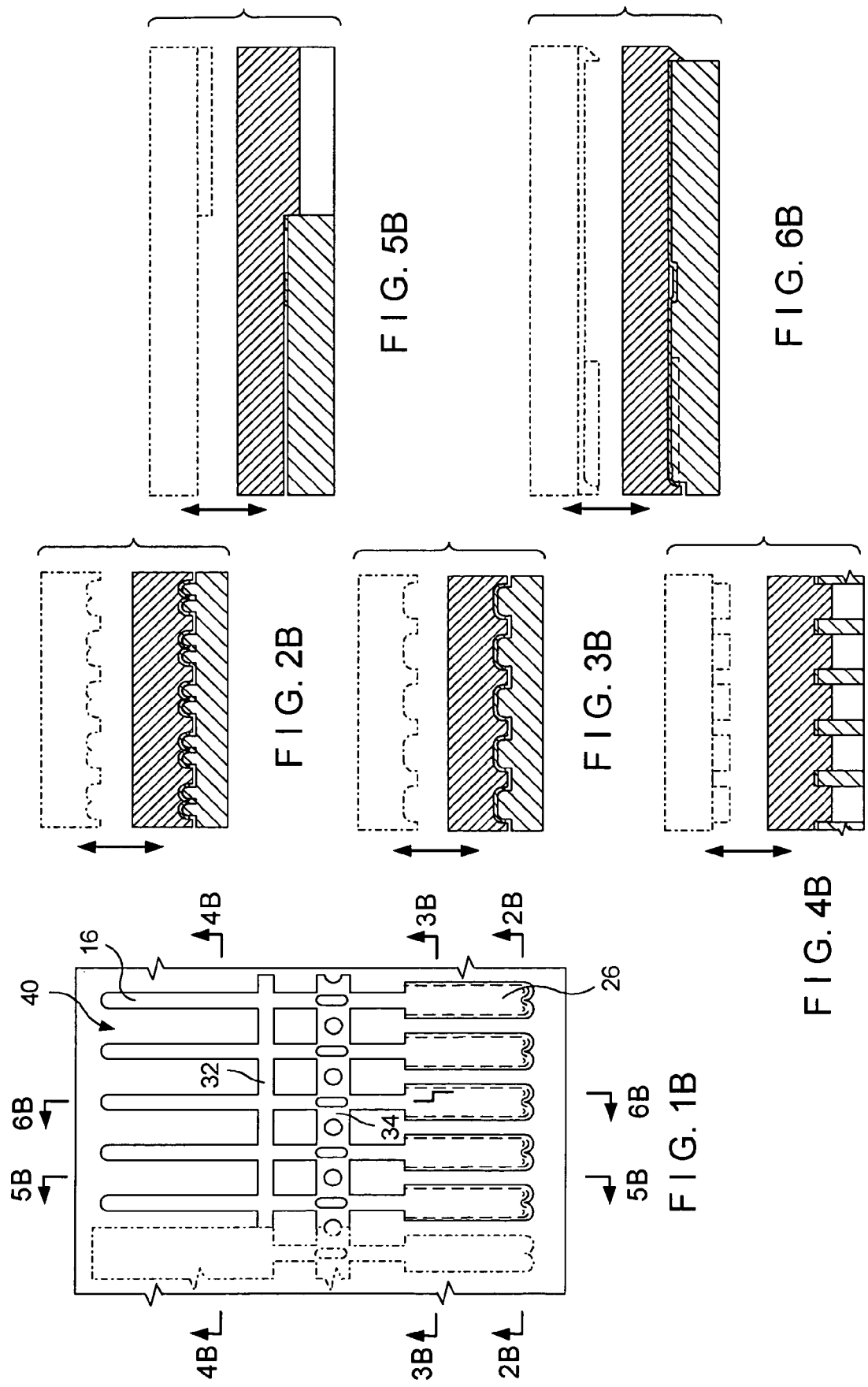

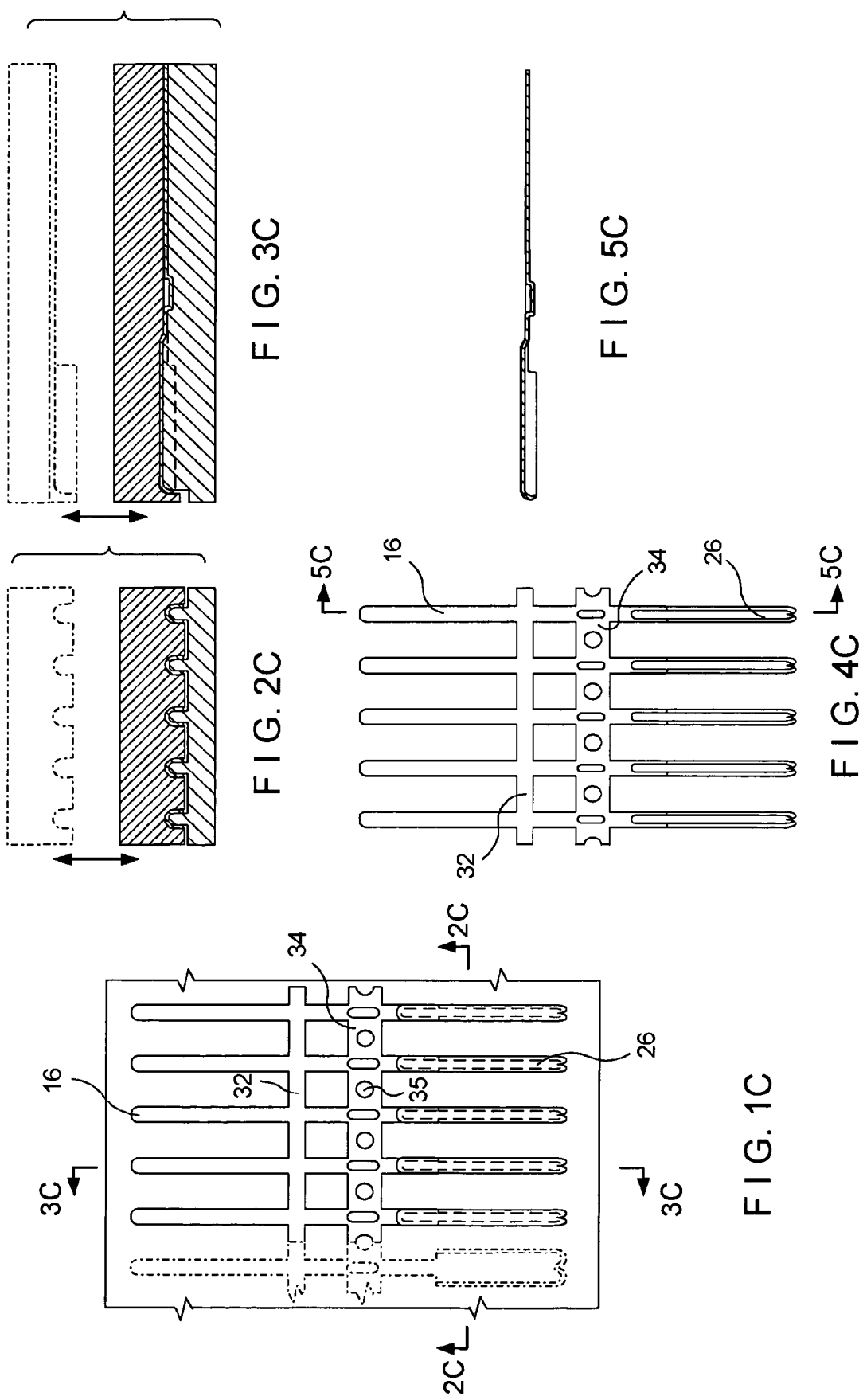

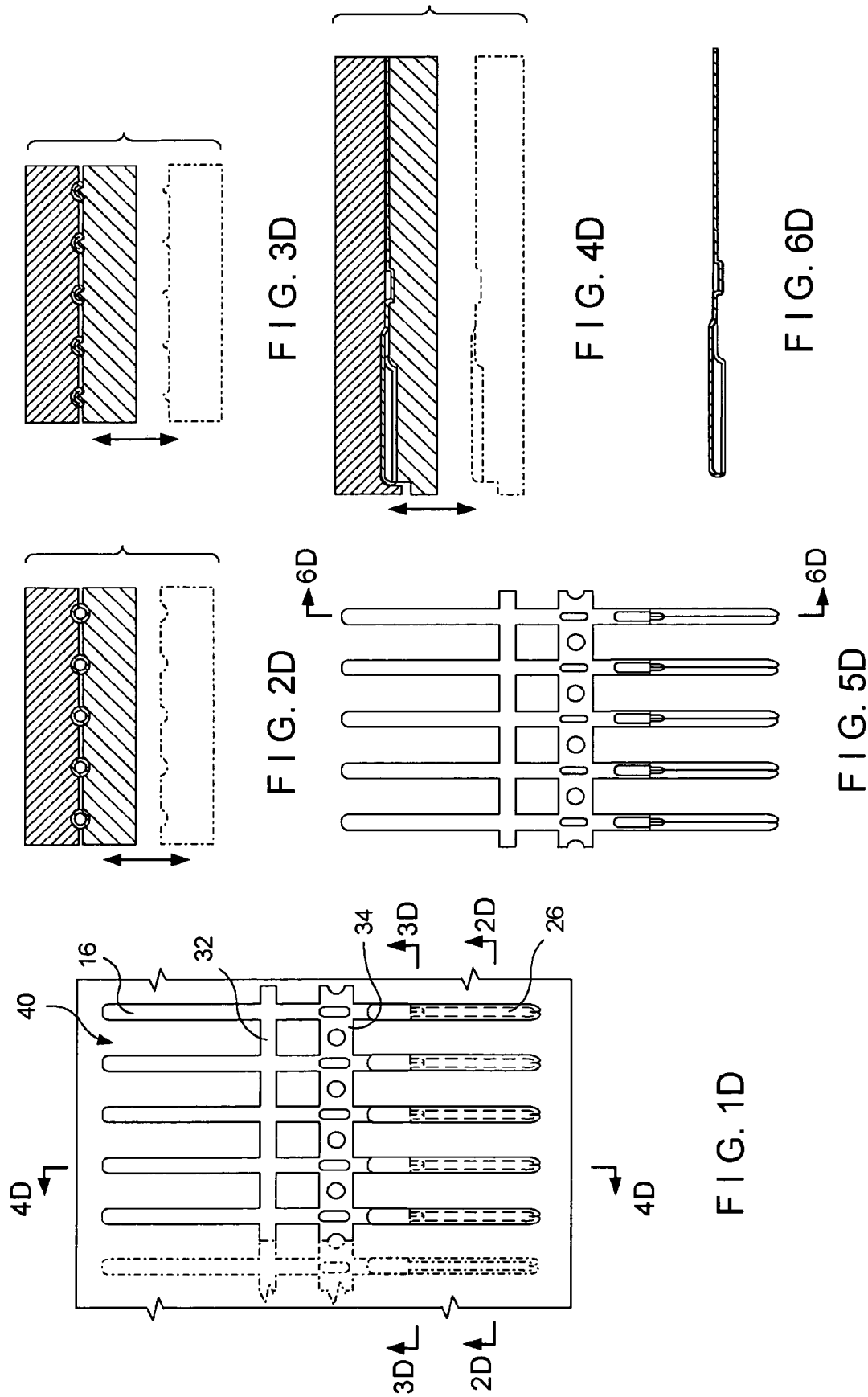

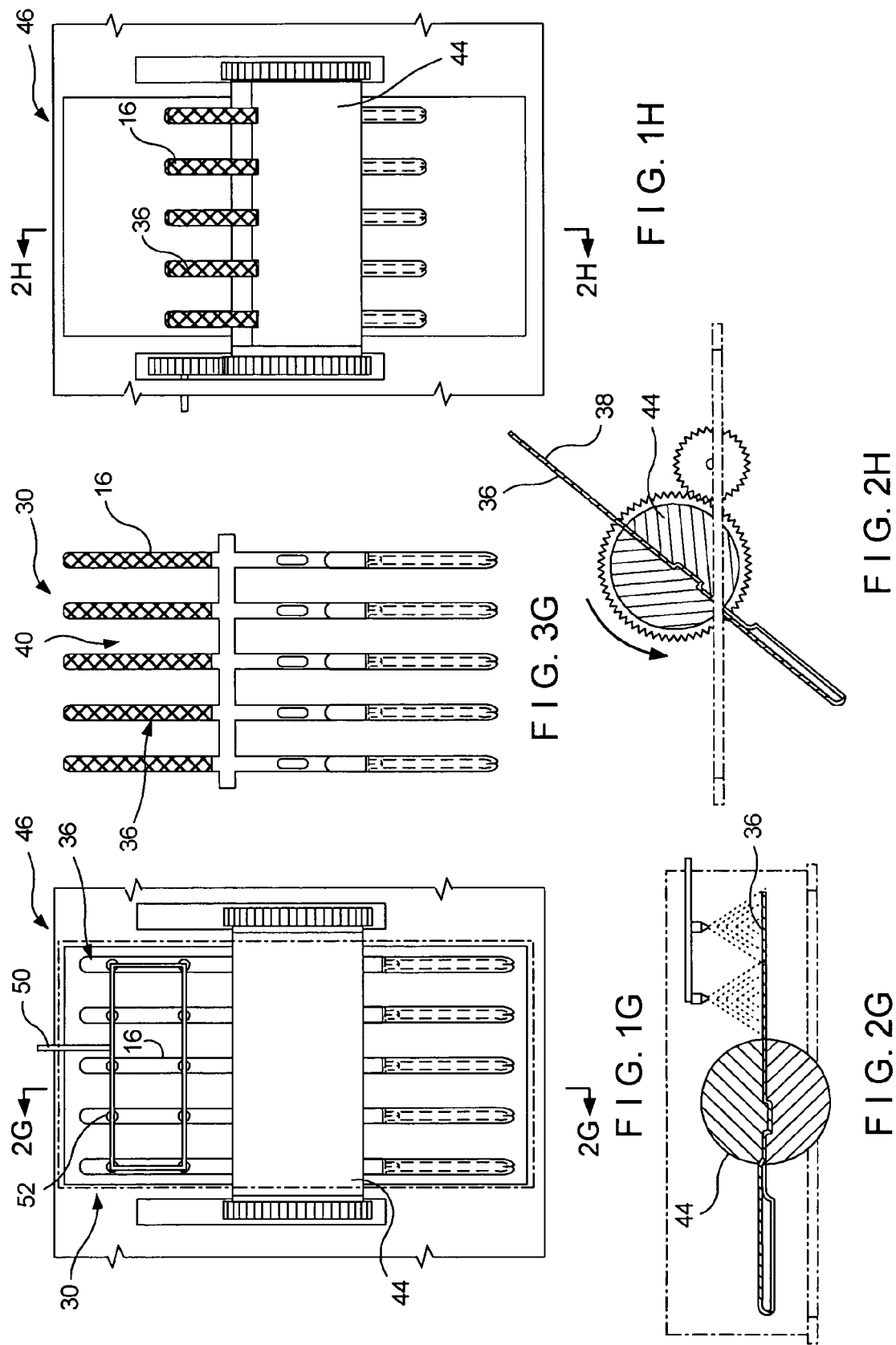

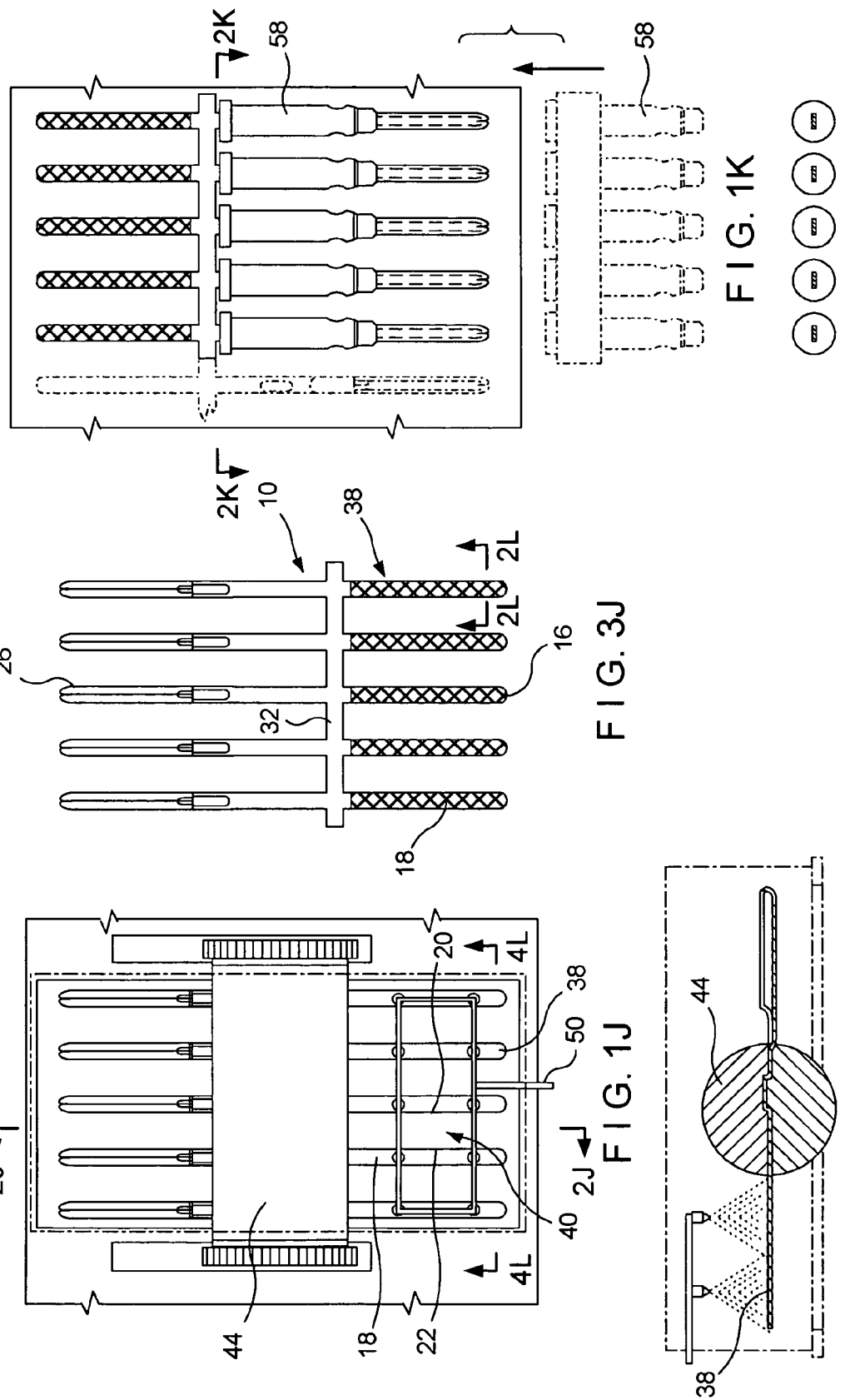

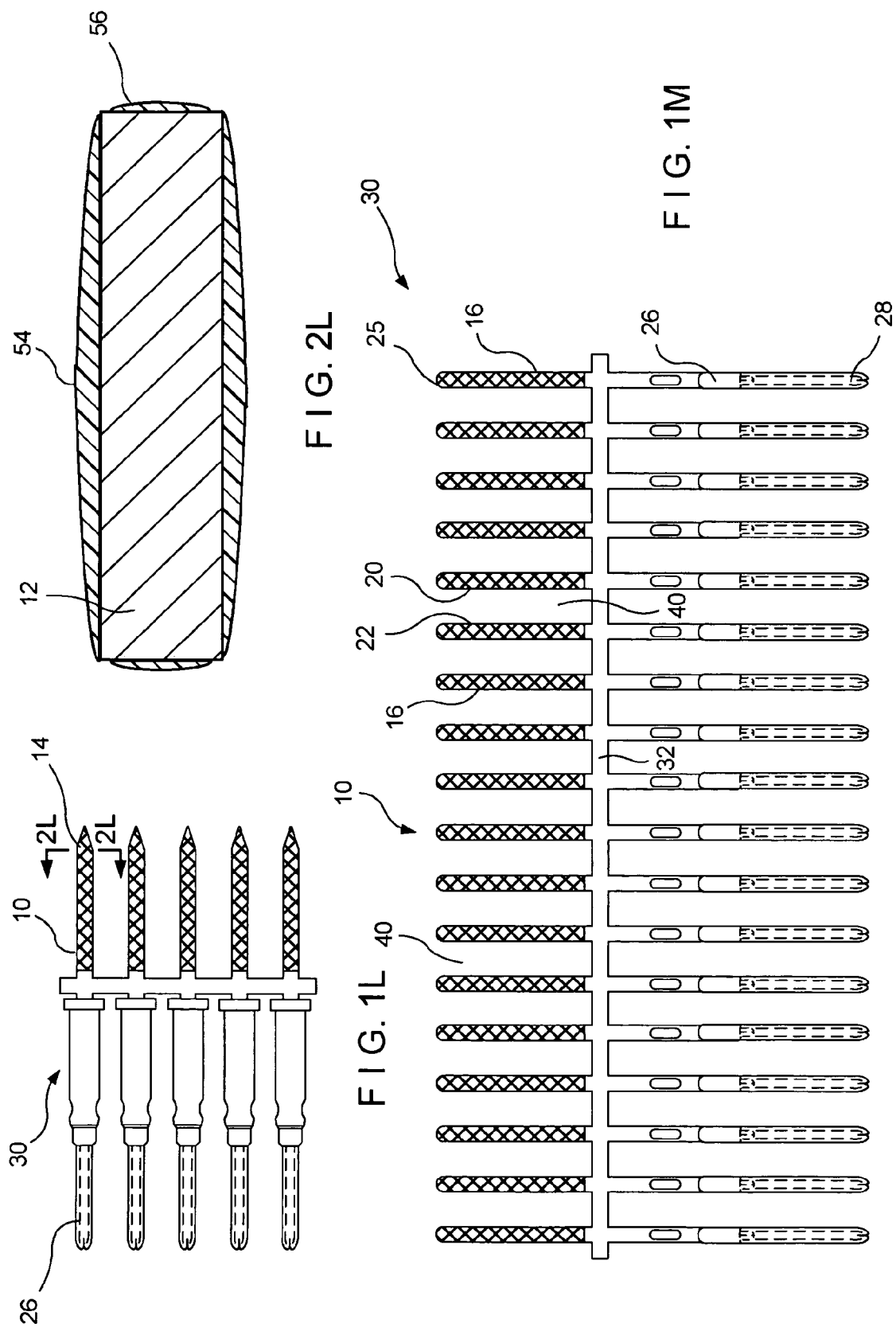

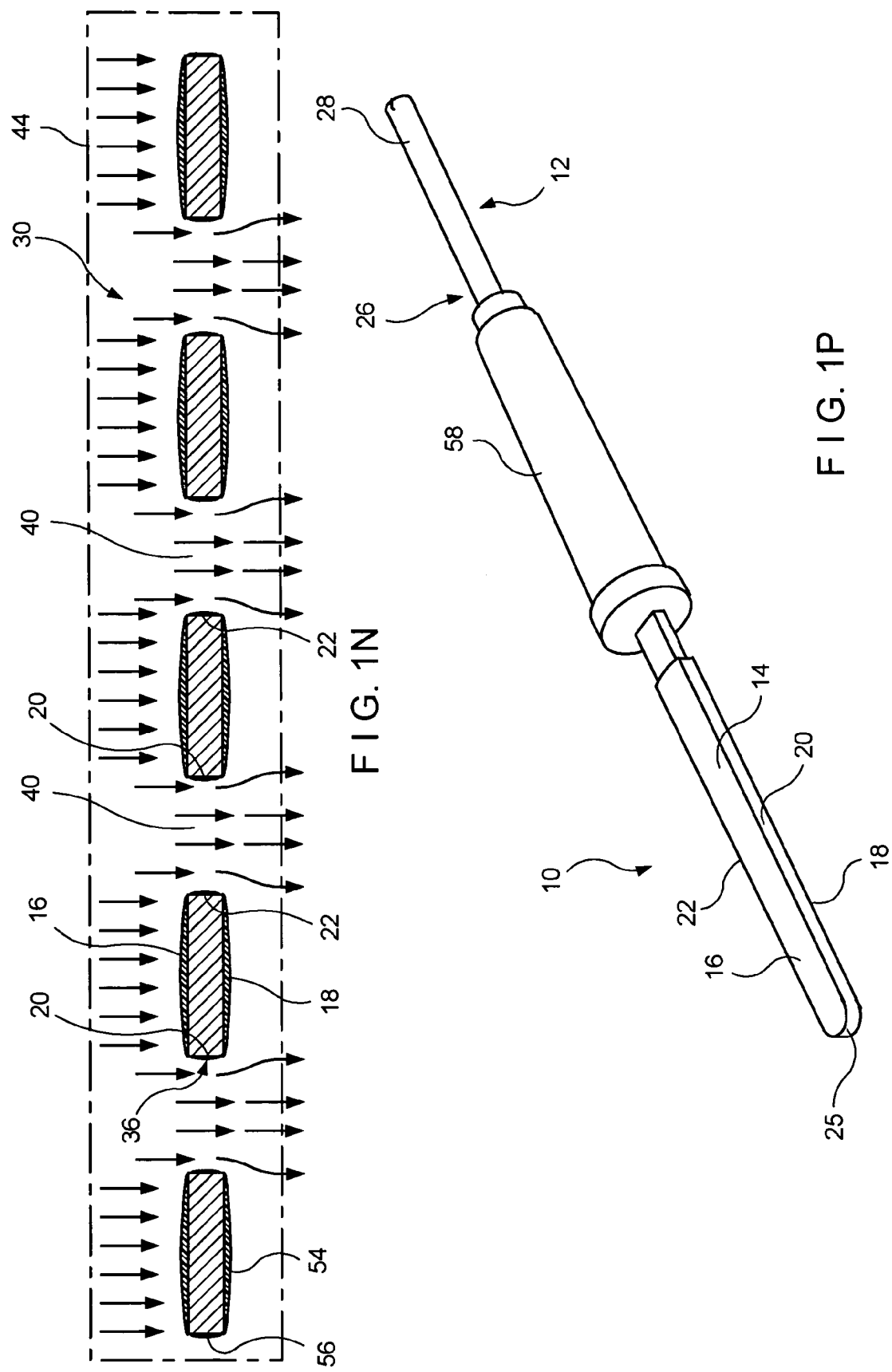

METHOD OF MANUFACTURING OF ELECTROSURGICAL IMPLEMENTS

FIELD OF THE INVENTION

The invention relates to the field of disposable electrosurgical blades or active electrodes used to perform electrosurgical procedures more particularly it relates to a method of manufacturing such blades.

BACKGROUND OF THE INVENTION

Electro-surgery is a method of using electric current to cut tissue. It is used for purposes such as removing lesions, controlling bleeding, or cutting tissue. Precise cuts can be made with limited blood loss. Electro-surgery is commonly used for in dermatological and surgical procedures. High frequency voltage, typically in the range of 400 kHz to 750 kHz is used in order to avoid stimulation of the nervous system which responds to low frequencies.

Electro-surgery is performed by connecting the electrosurgical blade or active electrode to an electrosurgical generator, activating the generator to supply current, and delivering the current through the blade and into tissue. A simple circuit is formed whereby current passes through the blade, into the tissue of the body, and out through another connection in the body such as a ground. The typical electrosurgical instrument is a metal blade with a very low level of resistance. The cell tissue has a high level of resistance. Due to the high resistance, heat builds up in the tissue causing individual cells to expand, explode, and burn away.

The blade is positioned in a pencil-like holder which the surgeon manipulates to achieve the desired effect at the surgical site. Selecting and adjusting the characteristics of the current delivered by the electrosurgical generator allows the surgeon to cut the tissue, to coagulate bleeding from the tissue, or to simultaneously cut and coagulate. The ability to control the application of electrical energy to the tissue to cut and coagulate tissue is one of the substantial advantages of electro-surgery, and such advantages contribute to the use of electro-surgery in most major surgical procedures.

The electrical power applied can vary from a few watts for delicate neurosurgical procedures to approximately 300 watts for cutting substantial tissues in open surgical procedures. The open circuit voltage prior to energy transfer into the tissue may be in the range of 5,000-10,000 volts peak to peak. The voltage drops substantially as the current flow increases through the highly resistive tissue. Typical tissue impedances range between about 10 ohms and 500 ohms.

The physical characteristics of a typical electrosurgical blade are important to carry out electro-surgery. The typical electrosurgical blade has two elongated broad, planar surfaces bisected by two narrow edges. The broad surfaces of the two broad sides are generally parallel and exist on opposite sides of the working area of the blade. The adjoining narrow edges extend between the broad sides and curve around a distal end or tip of the working area.

Cutting or coagulating is achieved by bringing the narrow edge into close proximity with the tissue. The current passes through the blade with little impedance and then through the narrow edge of the blade into the tissue. The narrow edges have a relatively small surface area causing high current Gaussian current density to flow through this area. The current is transferred into the tissue as relatively short arcs, thereby causing enough heat to explode or rupture the cells of the tissue at the interface with the narrow leading edge. The tissue separates at the leading edge leaving a well-defined incision. It is in this manner that the current from the electrosurgical blade cuts the tissue, rather than the tissue being separated from the physical contact and mechanical action of a sharp edge, as in traditional cutting procedures. The narrow edge of the typical electrosurgical blade is not sharp and cannot cut tissue as a result of mechanical action.

A significant drawback of the prior art is that blood and the innards of the bursting cells come in contact with and adhere to the surface of the electrosurgical blade. Although the impedance of the typically metal blade is far less than that of the tissue, it is still significant enough that the blade absorbs enough of the transferred energy to increase its temperature significantly during electro-surgery. The increased temperature of the blade causes the cell fluids, body fluids and blood to dehydrate, denature and accumulate on the blade in the form of a crust-like buildup. Unless periodically removed, the crust-like buildup increases as the blade is used. More particularly, charred and necrotized tissue and cells can be generated by localized excessive thermal heating, wherein such tissue and cells tend to adhere to the surgical instrument such as the cutting edge of a surgical knife. The presence of such tissue and cells on the working surface of the instrument interferes with subsequent cutting by disrupting the current field and correspondingly reduce the efficiency and efficacy of the instrument.

The crust-like buildup negatively affects the ability for the electrosurgical knife to function. To restore functionality the knife must be frequently cleaned. Doing so is only partially effective and is time consuming. Another alternative is to frequently replace the blades, but this adds cost and can also be time consuming. The buildup on the broad sides of the blade also has other negative consequences. The blade drags against the tissue at the incision and creates an undesirable "feel" when manipulating the instrument. Further, the crust obscures the ability for the surgeon to view the expected location of energy delivery from the blade into the tissue, decreasing the accuracy of the cut. These problem and consequences of the crust-like buildup on electrosurgical blades have been a long felt unsolved need in the art.

Various prior art methods have been devised in order to overcome the aforementioned problems by providing ways to minimize and remove the crust-like buildup. One approach in the art has been for the user to use a specifically-designed mechanical cleaning device into which the blade is inserted and withdrawn to scrape or otherwise remove the crust buildup. The mechanical scraping and cleaning techniques are generally not preferred by surgeons because scraping prolongs the surgical procedure. Moreover, scraping is generally not fully effective in removing all of the crust like material, but is better than doing nothing at all. Consequently, the necessity to scrape the blade during the surgical procedure has been tolerated by surgeons.

Another approach to avoid crust-like buildup on electrosurgical blades has been to coat the exterior of the blades with a nonstick coating. The nonstick coating minimizes the adherence of the crust-like materials. Since the broad sides of the blade attract the most buildup and are the primary location where the buildup normally occurs, it is ideal that the broad sides be coated. However, the narrow edges are primarily where the arcs of current flow from the blade to the tissue so it is important to have less or no coating on the narrow edges, so as not to impede the flow of current which would reduce the effectiveness of the device.

A variety of different types of release coating materials have been applied to electrosurgical blades. Among the types of release materials which have been used on electrosurgical blades are fluorinated hydrocarbon materials (similar to "Teflon"), silicone (polysiloxane), ceramic composites, paralyene polymers, and others. Among ceramic composites, thermally applied alumina (aluminum oxide—$Al_2O_3$) or alumina composite such as alumina-chromia, magnesium oxide, zirconia-yttria, and zirconia-calcia, are all known in the art. A preferred ceramic coating has a dielectric strength of at least 1,000 volts/mm in the frequency range of 500 kilohertz to 1 megahertz, more preferably at about 3,000 volts/mm. These substances have been used on electrosurgical blades primarily because of their nonstick characteristics. Other factors which influence the choice of such materials for coating electrosurgical blades involve biocompatibility, heat resistance, dielectric strength, and adherence.

Adherence is a particularly important characteristic, because the nonstick, release material should remain on the broad sides of the blade, despite the relatively high temperature of the metal blade and the occasional electrical arcing from the broad sides to the adjoining tissue. Because of the desire for good adherence, the typical approach has been to mechanically roughen the metal body prior to applying the release or nonstick coating. Mechanically roughening the surface of the metal body increases the surface area of the metal body by creating a large number of mechanical peak and valley aberrations into an otherwise smooth surface. The increased surface area and the texture of the peaks and valleys provide a complex mechanical structure to which the coating material will adhere with increased tenacity. Typical mechanical roughening techniques involve grit blasting, etching, burnishing, or knurling. Another roughening technique is to fuse a layer of textured material to the smooth surface. The fused textured material causes the release coating to adhere.

While the roughened surface achieves the objective of enhanced adherence of the release material, it also creates certain undesirable characteristics. Each of the peaks of the roughened surface presents a minuscule elevated point source from which an electrical field gradient exists when the metal body of the electrosurgical blade is energized with high voltage. These elevated points decrease efficiency. Field gradients are responsible for initiating arcs of the electrical energy and should come only from the narrow sides or tip of the blade. The corners where the broad sides join the narrow edges create the desirable field gradient locations for the initiation of the arcs to deliver the energy for cutting and coagulating as described above. Arcing from the points of the roughened broad sides of the blade may have the tendency to destroy the nonstick or release coating material on the broad sides by erupting the coating from the points where the arcs initiate from the peaks. Once the nonstick coating is destroyed, a knife with a rough surface having many field gradients is less effective than a smooth knife having no coating to start.

To overcome the above-noted problems related to destruction of the non-stick coating and multiple field gradients, various prior art improvements function by providing thick or multiple coats of nonstick material to the blade. Once the coating has been built up to a sufficient thickness, enough electrical insulation exists to eliminate or inhibit the arcing from the broad sides. However, applying multiple coats of material to the blade increases its manufacturing cost and decreases the conductivity of the blade. The width of the blade between the coatings on the broad sides is also increased by the added width of the multiple layers of coatings. The increased width creates excess drag on the adjoining tissue as the blade cuts.

It is known from the prior art to provide an electrosurgical blade having a working area with a single uniform layer coating of nonstick, release material comprising substantially silicone (polysiloxane) initially applied over and adhered to both the broad and narrow sides of the device. In order to use the device, a drawback is that the user must vaporize or scrape off the coating initially present on the narrow edges and at the corners in the vicinity of the tip. During the vaporization or scraping process, the coating ideally remains intact and smoothly adhered to the broad sides of the electrosurgical blade, although the edges of the coating and electrical gradient at these edges may not be smooth.

The uniformity in the cross-sectional thickness of the coating will vary slightly on the narrow edges due to forces acting on a decreased area. Surface tension, fluidity, and quicker solidifying times reduce the thickness at those corners.

The crust buildup is a pitfall of the electrosurgical procedure. The crust spaces the blade from the tissue and makes it difficult to transfer energy into the tissue so as to achieve the desired electrosurgical effect. A typical area for the crust buildup is the broad sides of the blades because most of the energy transferred is through a narrow edge during cutting. The energy transfer tends to keep the narrow edges clean. Consequently, the buildup of crust is on the broad sides of the blades and is the impediment to conducting electro-surgery.

SUMMARY OF INVENTION

One aspect of the invention provides a method of manufacturing electrosurgical implements, wherein each electrosurgical implement is defined by at least a distal working portion having two oppositely positioned broad planar sides bisected by two narrow edges. An integral module is formed consisting of a plurality of spaced from each other interconnected blades or implements. The implements are arranged in the module in such a manner that a multiplicity of narrow operational spaces are defined between facing each other narrow edges of each pair of the adjacent implements, whereas a coating is applied to the distal working portions of the implements forming a part of the module. A stream of coating is directed substantially normally to the broad planar sides of the distal working portion and substantially parallel to narrow edges of the implements arranged in the respective operational spaces.

As to still further aspect of the invention, upon passage of the stream of coating through the narrow operational spaces, a low pressure zone is being developed at the stream-module interface such low pressure zone causes increase in the velocity of the coating spray within the operational spaces resulted in the reduced adherence of the coating to the narrow edges of the implements.

As to still another aspect of the invention, each implement comprises a proximal shank portion connected to the distal working portion, wherein in the coating step at least a part of the shank portions is positioned within a receiving arrangement adapted for restrictive rotation. In coating step the coating is being initially applied to one broad planar side of the implements, then said holding device and the module are being rotated as to expose the second broad planar side of the respective implements to the flow of coating.

BRIEF DESCRIPTION OF THE DRAWINGS

FIG. 1B is a view showing another stamping step in the formation of the module of electrosurgical blades or implements;

FIG. 2B is a section view according to section line 2B-2B of FIG. 1B;

FIG. 3B is a section view according to section line 3B-3B of FIG. 1B;

FIG. 4B is a section view according to section line 4B-4B of FIG. 1B;

FIG. 5B is a section view according to section line 5B-5B of FIG. 1B;

FIG. 6B is a section view according to section line 6B-6B of FIG. 1B;

FIG. 1C is a view showing a further stamping step in the formation of the module of electrosurgical blades or implement;

FIG. 2C is a section view according to section line 2C-2C of FIG. 1C;

FIG. 3C is a section view according to section line 3C-3C of FIG. 1C;

FIG. 4C is an intermediate view of the module;

FIG. 5C is a section view according to section line 5C-5C of FIG. 4C;

FIG. 1D is a view illustrating still another stamping step in the formation of the module of electrosurgical blades or implements;

FIG. 2D is a view according to section line 2D-2D of FIG. 1D;

FIG. 3D is a section view according to section line 3D-3D of FIG. 1D;

FIG. 4D is a section view according to section line 4D-4D of FIG. 1D;

FIG. 5D is a further intermediate view of the module of electrosurgical implements of the invention;

FIG. 6D is a section view according to section line 6D-6D of FIG. 5D;

FIG. 1F is a view showing position of the module of electrosurgical implements within a holding device;

FIG. 1G is a view showing one position of the module within a coating chamber;

FIG. 2G is a section view according to section line 2G-2G of FIG. 1G;

FIG. 3G is a view of the module of the electrosurgical implements having a coating on one broad planar sides of the implements;

FIG. 1H illustrates movement of the module positioned within the holding device from one position to another;

FIG. 2H is a section view according to section line 2H-2H of FIG. 1H;

FIG. 1J illustrates another position of the module in the holding device positioned within the coating chamber;

FIG. 2J is a section view according to section line 2J-2J of FIG. 1J;

FIG. 3J is a view of the module having the coating on the other broad planar sides of the implements;

FIG. 1K illustrates the step of formation of the insulation sleeves on the shank portions of the module;

FIG. 2K is a section view according to section line 2K-2K of FIG. 1K;

FIG. 1L is a view of the module with insulation sleeves;

FIG. 2L is a section view according to section line 2L-2L of FIG. 1L;

FIG. 1M is a view of the module containing 18 electrosurgical blades or implements;

FIG. 1N is a schematic diagram showing the flow of the coating fluid during the coating step in the method of the invention; and FIG. 1P is a semiprospective view of the electrosurgical implement or blade.

DETAILED DESCRIPTION OF THE INVENTION

Figure 5A:
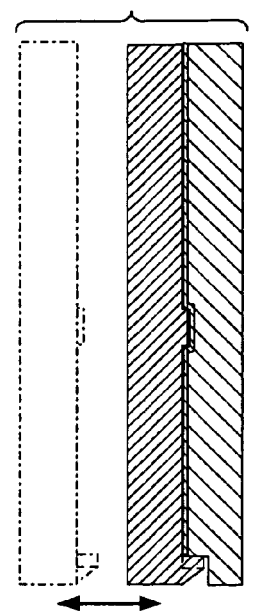
FIG. 5A is a section view according to section line 5A-5A of FIG. 1A.
Figure 6A:
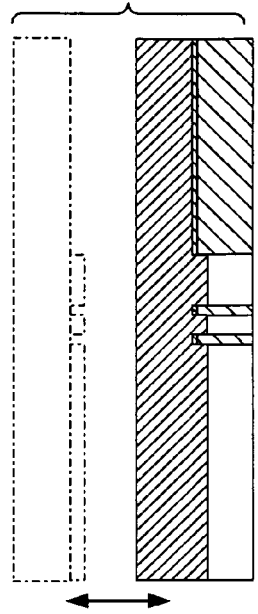
FIG. 6A is a section view according to section line 6A-6A of FIG. 1A.
Figure 2A:
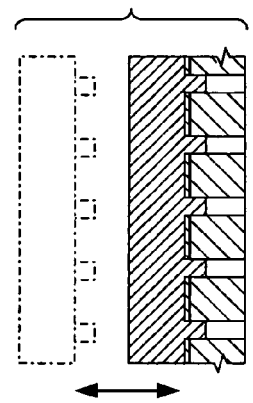
FIG. 2A is a section view according to section line 2A-2A of FIG. 1A.
Figure 3A:
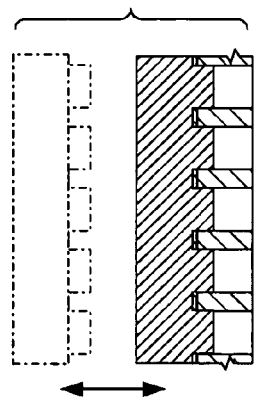
FIG. 3A is a section view according to section line 3A-3A of FIG. 1A.
Figure 4A:
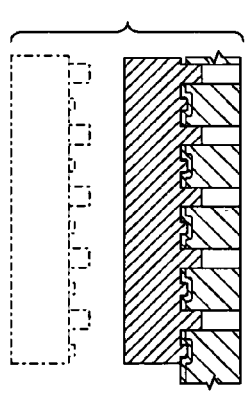
FIG. 4A is a section view according to section line 4A-4A of FIG. 1A.

Turning now to the drawings in general, and specifically to FIG. 1P best illustrating the electrosurgical blades or implements 10 which are typically produced from stainless steel or other metals. The electrodes, blade or implement has a body 12 which is formed in the conventional shape of a typical electrosurgical blade known in the art. In this manner, it includes a distal working area 14 portions which has two oppositely positioned broad planar sides 16 and 18 bisected by two narrow edges, 20 and 22. The narrow edges extending between the broad sides terminate at a distal end or tip 25 of the working area of any desired configuration. A cylindrically shaped proximal shank portion 26 forms a unitary structure with the distal working area 24 of each blade. The shank portion 26 terminates at the proximal end 28 which in use is adopted to fit within and connect to a standard collet or receptacle in a conventional electrosurgical handpiece.

Figure 1A:
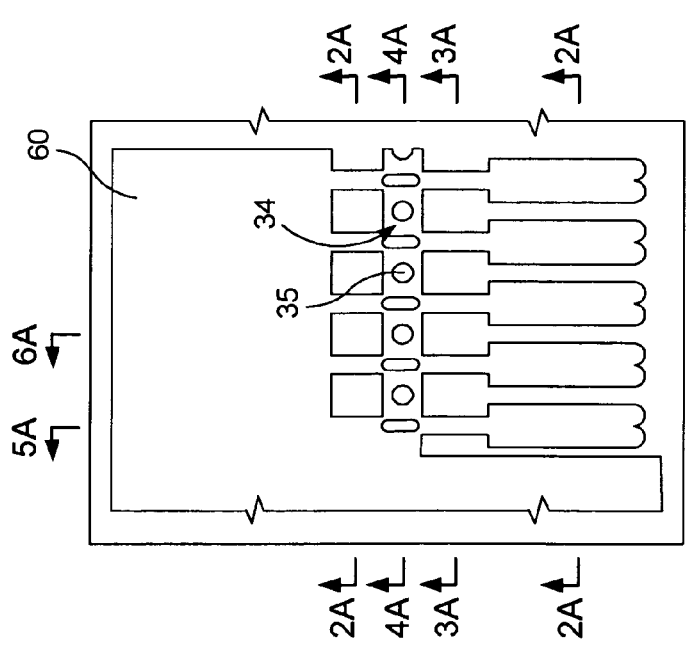
FIG. 1A is a view showing an initial stamping step in the formation of a module of electrosurgical blades or implements utilized in the method of the invention.
Figure 1E:
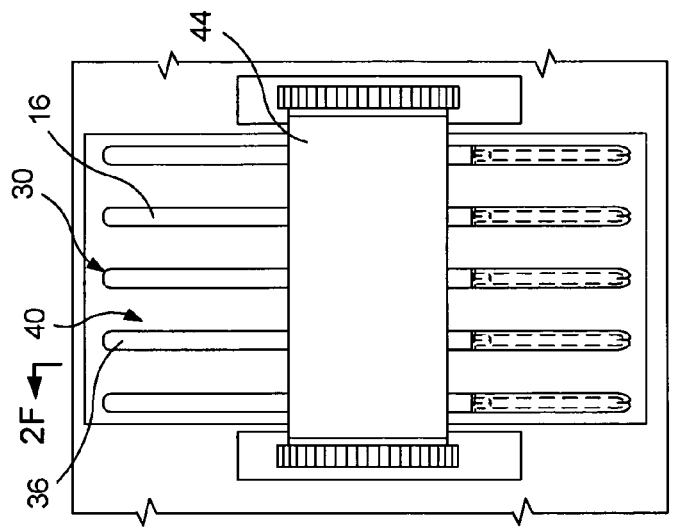
FIG. 1E is a view showing a still further stamping step in the formation of the module of electrosurgical blades or implements.
Figure 2F:
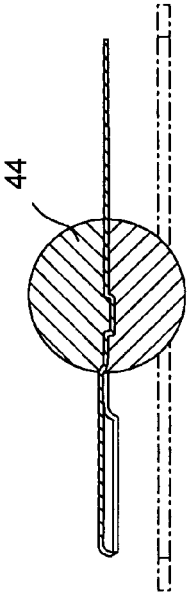
FIG. 2F is a section view according to section line 2F-2F of FIG. 1F.
Figure 2E:
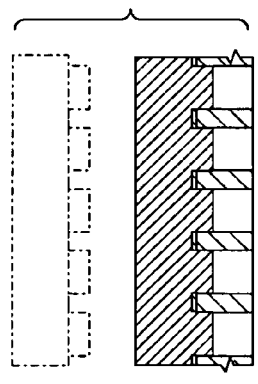
FIG. 2E is a section view according to section line 2E-2E of FIG. 1E.
Figure 1E:
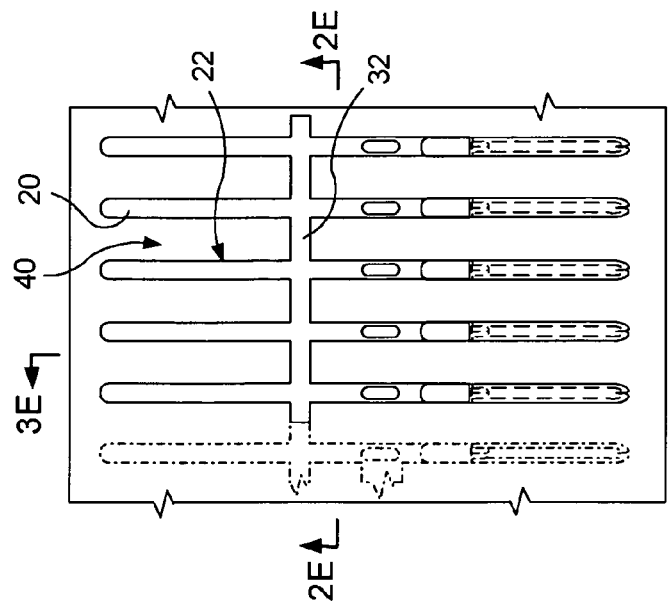
Figure 3E:
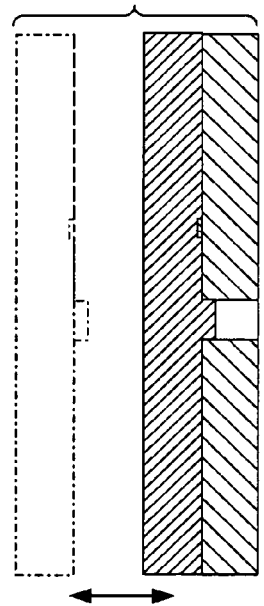
FIG. 3E is a section view according to section line 3E-3E of FIG. 1E.

Referring now to the FIGS. 1A, 2A, 3, 4A, 5A, 6A-1D, 2D, 3D, 4D, 5D and 6D illustrating the steps of a progressive stamping process utilized in the formation of an integral module 30 consisting of a plurality of spaced from each other electrosurgical blades, electrodes or implements 10. As shown in FIG. 1A a web 60 of flattened metal is provided so as to undergo the progressive stamping procedure. During the initial steps, a flattened periphery of the shank portion 26 of the implements, as well as a secondary connecting band 34 are defined with respective holes 35 being pierced. One of the functions of the secondary connecting band 34 is to facilitate transition of the metal web 60 from one stamping station to another. FIG. 2A-6A more specifically illustrate further steps in the stamping procedure, provided for the formation of elements of the module shown in FIG. 1A.

In the next stamping sequence, as illustrated in FIGS. 1B-6B, the implements of the module go through further transformation. More specifically, as clearly shown in FIG. 1B, in these stamping steps, the distal working portions 16 which are joined together by a primary connecting region or band 32 are formed. Furthermore, the proximal shank portions 26 are being converted from a flat to cylindrical-shaped members.

In the stamping steps illustrated in FIGS. 1C-5C and in 1D-6D the proximal shank portions 26 undergo further transformations to be formed as the cylindrically shaped members. The final steps of the stamping procedure are illustrated in FIGS. 1E-3E. The resulted integrated module 30 of the electrosurgical blades or implements 10 is best illustrated in FIGS. 1M, 1E, and 1L. According to one embodiment of the invention, an individual module 30 containing about eighteen implements 10 is being provided. It should be noted, however, that a module with any reasonable number of implements is within the scope of the invention. In the module, the upper or primary connecting region 32 formed during the stamping procedure interconnects the narrow edges 20, 22 of the adjacent implements. In this manner, an integrated, linear module 30 consisting of a plurality of spaced from each other implements is provided. A first face 36 of the module is defined by a multiplicity of broad, planar sides 16 of the interconnected implements. In a similar manner the second face 38 is defined by the opposite broad sides 18 of the implements. A plurality of operational spaces or gaps 40 is formed between the narrow edges of the adjacent blades. Thus, each operational space 40 is formed by two linear oriented, facing each other narrow edges 20, 22 of the adjacent blades, electrodes or implements.

The finally stamped modules 30 are then directed to the passivation process to preserve the steel and prevent corrosion. The passivation promotes oxidation or rust and then converts the oxidized metal to a metalophosphate through the use of phosphoric acid, thus providing a protective surface on the stainless steel. The resulted module has a silver matte finish and looks clean. After the passivation, the integrated module 30 are directed for the step of coating.

In one embodiment of the invention the electrosurgical electrodes or implements are coated with a dispersion of organic resin and PTFE. After this procedure the coated parts are dried at a specific temperature. Mid-cured at an accommodating temperature parts are cooled to a room temperature. A second dispersion coat is applied at a room temperature for a short period of time and then baked at 325° F. for a period of 15 minutes and fully cured at 600° F.

Referring now to FIGS. 1F, 2F, 1G-3G, 1H, 2H and 1J-3J illustrating in detail the coating steps of the method of the invention. To facilitate the steps of coating the integrated module 30 of the interconnected surgical implements is accommodated in the receiving device 44 arranged within a coating chamber 46 or any other suitable coating facility. As best illustrated in FIGS. 1G, 2G and in the initial position the module 30 is oriented in such a manner that the first face 36 thereof with the respective broad sides 16 of the implements is oriented substantially normally or perpendicular to the direction of the stream of coating delivered by a coating arrangement 50 having single or multiple nozzles 52. The nozzles 52 are calibrated to provide a uniform flow of coating along the entire width of the module. In this manner, a relatively thick layer of coating 54 is deposited on the broad sides of the implements.

Referring now to FIG. 1N, illustrating in substantial detail, the step of applying the liquefied coating to the module 30 during the coating procedure. The direction of flow of the coating is oriented substantially normally or perpendicular to the first face 36 of the module 30 including the first broad sides 16 of the implements situated within the receiving device 44. Significantly, in the method of the invention, during the coating process the limited surfaces of the narrow edges 20, 22 of the adjacent implements arranged in the respective operational spaces 40 to be substantially parallel to the coating stream direction. This is one of the factors preventing significant coating accumulation 56 on the narrow edges 20, 22 of the implements. In the embodiments where the adjacent narrow edges are positioned fairly close to each other to form narrow operational spaces 40. Due to the known principle of physics, the Venturi effect for example, upon passage of the stream of coating through the narrow operational spaces 40 a low pressure zone is being developed at the stream-module interfaces. This partial vacuum results in the greater velocity of the coating in the operational spaces 40 compared to that exposed to the broad sides 16, 18 of the implements. Thus, the flow of the applied coating is accelerated in the constricted area of the respective operational spaces 40. The higher the velocity the less time is needed for the coating fluid to pass through the respective operational spaces. This is resulted in a further reduced adherence of the applied coating to the narrow edges 20, 22 of the blades.

The nozzles 52 of the coating apparatus are typically calibrated to provide a uniform coating delivery over the entire first broad sides. As shown on FIGS. 1H and 2H, upon completion of the coating application to the first face 36, the receiving device 44 containing the module 30 is then rotated 180°, so as to expose the second face 38 thereof to the coating procedure. The coating process is then repeated (see FIGS. 1J-3J) in such a manner that the flow of coating is directed normally or at approximately 90° the other broad planar sides 18 of the implements. In both applications, the direction of coating fluid is substantially normal to the broad planar sides 16, 18 and also directed substantially parallel to the narrow edges 20, 22 of the implements arranged in the respective operational spaces 40. The holding device securely holds the respective module 30 at a predetermined and calibrated position with respect to the coating device 50. In this manner, the normal orientation of the coating fluid flow relative to the faces of the respective implement is assured. Since the narrow edges are arranged on the operational openings to be parallel to the coating stream direction, the coating deposits 56 on the narrow edges are minimal. Thus, both sides 36 and 38 of the module 30 are coated without removing or resetting its position within the coating chamber 46. This feature allows both sides to be treated in an identical manner, so that the coating will cure uniformly throughout the module. Due to the above-described arrangement, the thickness of the coating on the broad sides of the implements can be substantially increased if desired, without increasing the thickness of the coating on the narrow edges.

It is important that the thickness of the coating deposits 56 on the narrow edges 20, 20 be substantially limited. The present invention decreases the amount of coating 56 on the narrow edges allowing the surgical blades or implements to be used immediately, without the need for the traditional steps of scraping the coating off the narrow sides or conducting prolonged burning of the coating. The blades or implements may also have a thicker coating 54 on the broad sides than that of the prior art. This ensures that the coating last longer and maintains the nonstick release characteristics during surgical procedures. Thus, surgical procedures utilizing the present device are more efficient because the preparation time for use of each knife is decreased and a knife may be used for a longer period of time before cleaning or replacement is required.

As illustrated in FIGS. 1K and 2K the entire coated integrated module 30 undergoes the molding process, so as to simultaneously position plastic sleeves 58 around the shank portions of all implements. Then, the step of separation is carried out, wherein the module 30 is separated into the individual blades or implements 10 by removing the upper carrier or primary connecting region 32. In the final steps of the method the implements are sterilized and packed. The manufacturing cycle is completed when the sterilized electrosurgical blades or implements are directed for storage and then for further handling and distribution.

The method of manufacturing electrosurgical implements of the invention has been described and illustrated with reference to specific embodiments of the invention as illustrated in the figures of the drawings. However, it should be noted that any obvious modifications of the method which are obvious to a person of ordinary skill in the present art are within the scope of the invention. For example, the holding device illustrated in FIGS. 1F, 2F, 1G, 2G, 1H, 2H, etc. is shown having a horizontally oriented axis of rotation. On the other hand, it should be noted that the holding device containing the module of a plurality of implements and having a vertical axis of rotation is within the scope of the invention. Furthermore, the actual design of the holding device, as well as orientation of the nozzles different from that disclosed hereinabove is also contemplated.

What is claimed is:

1. A method of manufacturing electrosurgical implements, wherein each electrosurgical implement is defined by at least a distal working portion having first and second oppositely positioned broad planar sides bisected by two narrow edges, said method comprising the steps of
    formation of an integral module consisting of a plurality of the spaced from each other interconnected implements, said implements are being arranged in the module in such a manner that an operational space is defined between each said implement such that said narrow edges of each pair of adjacent implements face each other; and
    applying a coating to said distal working portions of the implements forming a part of said module.

2. The method according to claim 1, wherein each said electrosurgical implement comprises a proximal shank portion, said method further comprising the step of formation of insulation sleeves on said proximal shank portions of the implements, wherein said insulation sleeves are being formed simultaneously on all said shank portions of the module.

3. The method according to claim 2, wherein said insulation sleeves are being formed on said proximal shank portions by molding.

4. The method according to claim 1, wherein in said step of applying the coating, the coating is directed substantially normally to said broad planar sides of the distal working portion and substantially along the narrow edges of the implements arranged in respective operational spaces.

5. The method according to claim 4, further comprising a step of passivation conducted prior to said step of applying the coating, wherein, the entire module containing said plurality of the implements is being passivated.

6. The method according to claim 4, wherein said integral module further comprises a connecting region interconnecting said distal working portions of the implements, said method further comprises a step of separation, wherein said module is separated so as to form the individual implements by removing said connecting region.

7. The method according to claim 4, wherein in said step of applying the coating, an amount of coating deposits on the narrow edges of the implements in the module is substantially reduced comparative to an amount of coating deposits on the broad planar sides of the implements.

8. The method according to claim 4, wherein said coating is applied in a form of a stream, upon passage of the stream of applied coating through the operational spaces, a low pressure zone is being developed at said operational spaces.

9. The method according to claim 8, wherein said low pressure zone causes increase in the velocity of the stream of applied coating within said operational spaces.

10. The method according to claim 8, wherein each said implement forming a part of said module further comprises a proximal shank portion connected to the distal, working portion, wherein in said coating step at least a part of said shank portions is positioned within a receiving arrangement adapted for restrictive rotation.

11. The method according to claim 10, wherein in said step of applying in the coating, the coating is being initially applied to said first broad planar sides of said implements, then said receiving arrangement and the module are being rotated as to expose said second broad planar sides of the respective implements of the module to said stream of applied coating.

12. The method according to claim 11, wherein said receiving arrangement and said module are being rotated 180°.

13. The method according to claim 8, wherein in said step of applying the coating, said stream of applied coating is uniformally applied throughout the entire width of the module.

14. A method of manufacturing electrosurgical implements, wherein each electrosurgical implement is defined by at least a distal working portion having first and second oppositely positioned broad planar sides bisected by two narrow edges, said method comprising the steps of:
    formation of an integral module consisting of a plurality of the spaced from each other interconnected implements, said implements are being arranged in the module in such a manner that an operational spaces is defined between each said implement such that said narrow edges of each pair of adjacent implements face each other; and
    applying a coating to said distal working portions of the implements forming a part of said module, so that said coating is directed substantially normally to said broad planar sides of the distal working portions and substantially along the narrow edges of the implements arranged in respective operational spaces of the module, so as to reduce an amount of coating deposits on the narrow edges of the implement of the module.

15. The method according to claim 14, wherein each said implement forming a part of said module further comprises a proximal shank portion connected to the distal working portion, wherein in said step of applying the coating at least a part of said shank portions is positioned within a receiving arrangement adapted for restrictive rotation.

16. The method according to claim 15, wherein said coating is being initially applied to all said first broad planar sides of said implements, then said receiving arrangement and the module are being rotated so as to expose all said second broad planar sides of the implements of the module to said coating.

17. The method according to claim 16, wherein said receiving arrangement and said module are being rotated 180°.

18. The method according to claim 14, wherein said coating is a stream of coating, so that in said step of applying the coating said stream of coating is uniformally applied throughout the entire width of the module.

19. The method according to claim 14, further comprising a step of passivation conducted prior to said step of applying the coating, wherein, the entire module containing said plurality of, the implements is being passivated.

20. The method according to claim 14, wherein each said electrosurgical implement comprises a proximal shank portion, said method further comprising the step of formation of insulation sleeves on said proximal shank portions of the implements, wherein said insulation sleeves are being formed simultaneously on all said shank portions of the module.

* * * * *